United States Patent
Borja et al.

(10) Patent No.: US 9,931,202 B2
(45) Date of Patent: Apr. 3, 2018

(54) DUAL OPTIC, CURVATURE CHANGING ACCOMMODATIVE IOL HAVING A FIXED DISACCOMMODATED REFRACTIVE STATE

(71) Applicant: NOVARTIS AG, Basel (CH)

(72) Inventors: David Borja, Suwannee, GA (US); Stephen J. Collins, Fort Worth, TX (US); William J. S. Dolla, Plano, TX (US); Jian Liu, Arlington, TX (US); Sudarshan Singh, Euless, TX (US); Douglas B. Wensrich, Bedford, TX (US)

(73) Assignee: Novartis AG, Basel (CH)

( * ) Notice: Subject to any disclaimer, the term of this patent is extended or adjusted under 35 U.S.C. 154(b) by 67 days.

(21) Appl. No.: 15/064,363

(22) Filed: Mar. 8, 2016

(65) Prior Publication Data

US 2017/0258581 A1 Sep. 14, 2017

(51) Int. Cl.
*A61F 2/16* (2006.01)

(52) U.S. Cl.
CPC .......... *A61F 2/1648* (2013.01); *A61F 2/1635* (2013.01); *A61F 2002/169* (2015.04); *A61F 2002/1682* (2015.04); *A61F 2002/16901* (2015.04); *A61F 2250/0003* (2013.01)

(58) Field of Classification Search
CPC .... A61F 2/1648; A61F 2/1635; A61F 2/1613; A61F 2/1624; A61F 2/1629; A61F 2/16; A61F 2002/1681; A61F 2002/169; A61F 2002/16901; A61F 2002/1682; A61F 2250/0003
See application file for complete search history.

(56) References Cited

U.S. PATENT DOCUMENTS

| | | | |
|---|---|---|---|
| 6,488,708 B2 * | 12/2002 | Sarfarazi | A61F 2/1613 623/6.34 |
| 9,090,033 B2 * | 7/2015 | Carson | A61F 2/1635 |
| 2004/0082993 A1 * | 4/2004 | Woods | A61F 2/1613 623/6.28 |

(Continued)

FOREIGN PATENT DOCUMENTS

| | | |
|---|---|---|
| WO | 2010/0010565 A2 | 1/2010 |
| WO | 2015/0148673 A1 | 10/2015 |
| WO | 2016/0140708 A1 | 9/2016 |

*Primary Examiner* — David H Willse
*Assistant Examiner* — Tiffany Shipmon

(57) ABSTRACT

An IOL includes a fluid optic body having a cavity defined by a sidewall, a deformable optical membrane intersecting the sidewall around an anterior circumference of the sidewall, and a posterior optic intersecting the sidewall around a posterior circumference of the sidewall. The posterior optic includes a central protrusion extending anteriorly into the cavity and the deformable optical membrane includes a ring-shaped protrusion extending posteriorly into a space between the sidewall and the central protrusion. A second optic body is spaced apart from the fluid optic body and coupled thereto via a plurality of struts. Axial compression causes the plurality of struts to deform the sidewall in a manner that increases the diameter of the cavity, modifying a curvature of the deformable optical membrane is modified. Contact between the ring-shaped protrusion and the central protrusion defines a maximum modification to the curvature of the deformable optical membrane.

16 Claims, 10 Drawing Sheets

(56) References Cited

U.S. PATENT DOCUMENTS

| | | | |
|---|---|---|---|
| 2005/0131535 A1* | 6/2005 | Woods | A61F 2/1613 |
| | | | 623/6.37 |
| 2007/0088433 A1 | 4/2007 | Esch et al. | |
| 2012/0075710 A1* | 3/2012 | Pugh | G02B 1/04 |
| | | | 359/665 |
| 2014/0180403 A1* | 6/2014 | Silvestrini | A61F 2/1635 |
| | | | 623/6.4 |
| 2016/0030161 A1 | 2/2016 | Brady et al. | |

\* cited by examiner

DUAL OPTIC, CURVATURE CHANGING ACCOMMODATIVE IOL HAVING A FIXED DISACCOMMODATED REFRACTIVE STATE

FIELD

This present disclosure relates generally to the field of intraocular lenses (IOLs) and, more particularly, to a dual optic, curvature changing accommodative IOL having a fixed disaccommodated refractive state.

BACKGROUND OF THE DISCLOSURE

The human eye in its simplest terms functions to provide vision by receiving light through a clear outer portion called the cornea, and focusing the image by way of a crystalline lens onto a retina. The quality of the focused image depends on many factors including the size and shape of the eye, and the transparency and focal power of the cornea and the lens.

When age or disease causes the lens to become less transparent, vision deteriorates because of the diminished amount of light that is transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

In the natural lens, bifocality of distance and near vision is provided by a mechanism known as accommodation. The natural lens, early in life, is soft and contained within the capsular bag. The bag is suspended from the ciliary muscle by zonules. Relaxation of the ciliary muscle applies a radial force that tightens the zonules, and stretches the capsular bag. As a result, the natural lens tends to flatten. Tightening of the ciliary muscle relaxes the tension on the zonules, allowing the capsular bag and the natural lens to assume a more rounded shape. In this way, the natural lens can focus on both near and far objects.

As the lens ages, it becomes harder and is less able to change shape in response to movements of the ciliary muscle. This makes it harder for the lens to focus on near objects, a medical condition known as presbyopia. Presbyopia affects nearly all adults by the age of 45 or 50.

When a cataract or other disease requires the removal of the natural lens and replacement with an artificial IOL, the IOL typically is a monofocal lens that provides a suitable focal power for distance vision but requires the use of a pair of spectacles or contact lenses for near vision. Multifocal IOLs, e.g., relying on diffractive patterns to general multiple foci, have been proposed but to date have not been widely accepted.

Therefore, a need exists for a safe and stable accommodative intraocular lens that provides accommodation over a broad and useful range.

SUMMARY OF THE DISCLOSURE

The present disclosure concerns curvature-changing, accommodative intraocular lenses (IOLs) that may be implanted in the capsular bag of a patient's eye and configured to harness the energy of the movement of the capsular bag upon contraction and relaxation of the ciliary muscles. In certain embodiments, the IOLs described herein are designed such that axial compression of the capsular bag changes the shape of a fluid optic (e.g., a fluid-filled cavity defined in part by a deformable optical membrane), thereby altering the curvature of the membrane and the power of the optic. As just one example, the IOLs described herein may include a fluid optic body and a second optic body each disposed on the optical axis and configured to be in contact with a surface of the capsular bag, the fluid optic body and the second optic body being coupled via a plurality of struts.

Upon axial compression of the capsular bag, an axial compressive force on the struts (e.g., via the posterior optic) may cause the struts to deform (e.g., to pivot or to bow out), resulting in an increase in the tension on the deformable optical membrane (i.e., the deformable optical membrane may stretch radially). As a result, the curvature of the deformable optical membrane may be reduced, as in a disaccommodated native lens. In addition, a mechanical block feature may define a maximum amount of radial stretching of the deformable optical membrane, thereby defining a consistent minimum optical power for the IOL.

Conversely, when axial compression is relaxed, the deformation of the struts may be relieved and the deformable optical membrane may become more rounded to provide for close vision, as in an accommodated native lens. For example, the plurality of struts can be biased to rotate in a direction opposed to the first direction upon relaxation of the axial compression. In accordance with various aspects of the present teachings, the IOLs described herein can be implanted into the native capsular bag to replace a cataractous or presbyopic natural crystalline lens removed therefrom.

In certain embodiments, an IOL includes a fluid optic body having a cavity defined by a sidewall, a deformable optical membrane intersecting the sidewall around an anterior circumference of the sidewall, and a posterior optic intersecting the sidewall around a posterior circumference of the sidewall. The posterior optic includes a central protrusion extending anteriorly into the cavity and the deformable optical membrane includes a ring-shaped protrusion extending posteriorly into a space between the sidewall and the central protrusion. A second optic body is spaced apart from the fluid optic body and coupled thereto via a plurality of struts. Axial compression causes the plurality of struts to deform the sidewall in a manner that increases the diameter of the cavity, modifying a curvature of the deformable optical membrane is modified. Contact between the ring-shaped protrusion and the central protrusion defines a maximum modification to the curvature of the deformable optical membrane.

Certain embodiments of the present disclosure may provide an IOL that has a relatively small size and/or occupies a limited volume of the capsular bag while still providing a substantial power change between its accommodated and disaccommodated state. Accordingly, the presently disclosed IOL may allow for smaller surgical incisions during implantation. Additionally, the shape and/or stiffness of certain embodiments of the presently disclosed IOL may allow for interaction of the IOL with the capsule in a manner that prevents posterior capsule opacification (PCO) and anterior capsule opacification (ACO) via square edge optics, open capsule, and mechanical procedure.

In addition, the mechanical block feature of the IOL (including the central protrusion portion of the posterior optic and the ring-shaped protrusion extending from the deformable optical membrane) may advantageously define a consistent minimum optical power for the IOL as well as increase the rate of power change at low levels of compression. Additionally, the increased rigidity around the perimeter of the deformable optical membrane provided by the ring-shaped protrusion may reduce spherical aberrations induced by the stretching of the deformable optical membrane during power change.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

The skilled person in the art will understand that the drawings, described below, are for illustration purposes only. The drawings are not intended to limit the scope of the applicant's teachings in any way.

DETAILED DESCRIPTION

Figure 1:
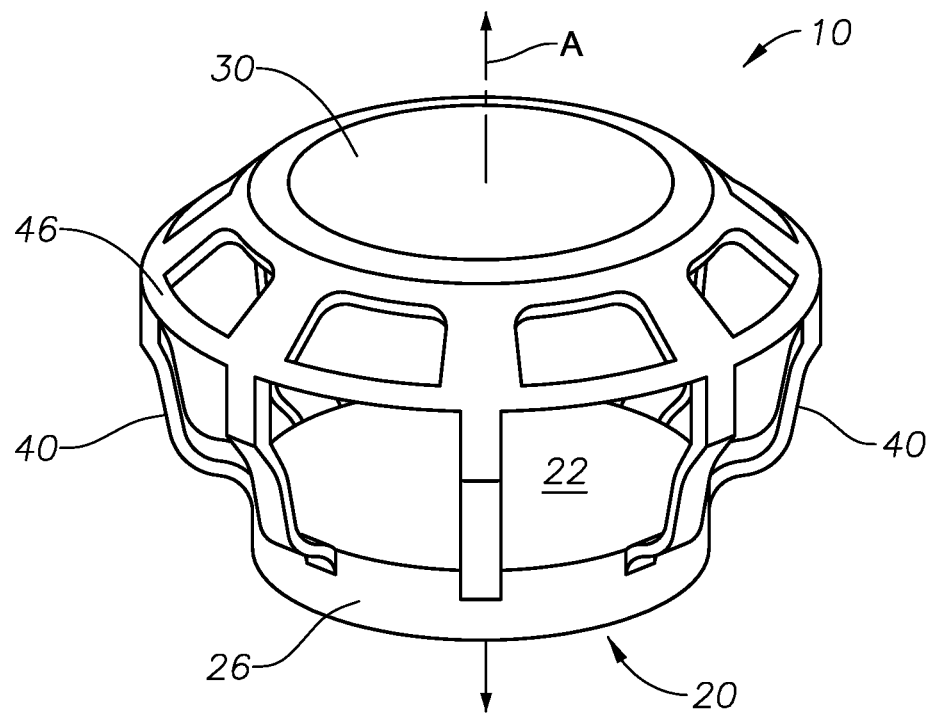
FIG. 1 is a perspective view of an exemplary curvature-changing, accommodative intraocular lens, according to certain embodiments of the present disclosure.
Figure 2:
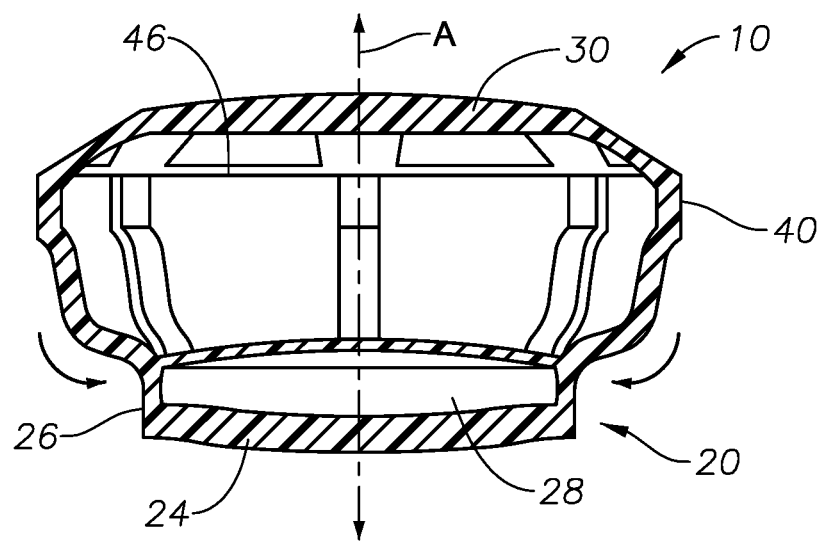
FIG. 2 is a cross-sectional view of the exemplary lens of FIG. 1.

The present disclosure generally relates to an intraocular lens (IOL) configured to be implanted in the capsular bag of a patient and that can utilize the movement of the capsular bag to change the power of the IOL. With reference to FIGS. 1 and 2, an exemplary IOL 10 is depicted, according to certain embodiments of the present disclosure. As shown in FIG. 1, the IOL 10 generally comprises a fluid optic body 20 and a second optic body 30 separated a distance apart. A plurality of struts 40 extend between the fluid optic body 20 and the second optic body 30 and couple the fluid optic body 20 to the second optic body 30, thereby defining a central space. In certain embodiments, another lens (e.g., as a solid lens) may be disposed in this central space, as discussed in detail below. When the IOL 10 is implanted within the capsular bag of a patient's eye such that the fluid optic body 20 and second optic body 30 are disposed on the optical axis (A) (allowing light traversing the IOL 10 to be refracted by fluid optic body 20 and/or second optic body 30), the compression of the capsular bag during disaccommodation can cause the plurality of struts 40 to deform (e.g., rotate, flex, bend, bow out) in manner that changes the shape of the fluid optic body 20, thereby altering the optical power of the IOL 10.

The fluid optic body 20 of IOL 10 can have a variety of configurations but generally comprises a sealed cavity for containing an optical fluid, the sealed cavity being at least partially defined by a deformable optical membrane. As best shown in FIG. 2, the fluid optic body 20 comprises a deformable optical membrane 22, a posterior optic 24, and a circumferential sidewall 26 extending therebetween such that a sealed cavity 28 (which may contain an optical fluid) is formed within the fluid optic body 20. As discussed in detail below, the sidewall 26 can be coupled to the deformable optical membrane 22 such that rotation/flexion of at least a portion of the sidewall 26 (e.g., due to movement of the struts 40) increases tension on the deformable optical membrane 22. In certain embodiments, the posterior optic 24 may be more rigid than the deformable optical membrane 22 so as to provide a relatively rigid surface upon which the axial force can be applied during compression of the capsular bag. For example, the posterior optic 24 may be formed from a stiffer (e.g., less elastic) material than deformable optical membrane 22. Alternatively, the posterior optic 24 may be formed of the same material deformable optical membrane 22 but may have an increased thickness relative to deformable optical membrane 22.

In certain embodiments, the junction of the posterior optic 24 and the sidewall 26 can be a relatively-sharp edge (e.g., the surfaces may be substantially perpendicular to one another) so as to create a discontinuous capsular bend at this junction during compression of the capsular bag. Likewise, such a discontinuous bend can be generated at the anterior portion of the IOL 10, for example, via a circumferential lip about the anterior optic body 30.

Although the deformable optical membrane 22 is depicted and described herein as being located anterior to the posterior optic 24 when disposed within the capsular bag 2 (such that the posterior optic 24 contacts at least a portion of a posterior surface 6 of the capsular bag 2), the present disclosure contemplates that an IOL 10 may alternatively be configured such that, when implanted within the capsular bag 2, the deformable membrane 22 may be located posterior to the deformable membrane 22 (such that the posterior optic 24 contacts at least a portion of an anterior surface 4 of the capsular bag 2).

The second optic body 30 of IOL 10 may include any suitable optic body facilitating the functionality described herein. For example, as depicted in FIGS. 1-2, second optic body 30 may comprise a solid (i.e., second optic body 30 may lack a cavity). As a result, second optic body 20 may provide a relatively rigid surface upon which the axial force during compression of the capsular bag may be applied. As another example, second optic body 30 may comprise a fluid optic similar to fluid optic body 20. In other words, IOL 10 may comprise both an anterior fluid optic (e.g., second optic body 30) and a posterior fluid optic (e.g., fluid optic body 20) each of which comprises a deformable optical membrane that changes shape upon axial compression of the capsular bag.

The fluid optic body 20 and the second optic body 30 of IOL 10 may each comprise a variety of materials that include, for example, fluid impermeable and biocompatible materials. In particular, the deformable optical membrane 24 and the posterior optic 24 may each be constructed of materials that are optically transparent and smooth (e.g., an optical-quality surface). Exemplary materials include, hydrogels, silicones, acrylic materials, and other elastomeric polymers and soft plastics. For example, the silicone materials can be unsaturated terminated siloxanes, such as vinyl terminated siloxanes or multi-vinyl terminated siloxanes. Non-limiting examples include vinyl terminated diphenylsiloxane-dimethylsiloxane copolymers, vinyl terminated polyphenylmethylsiloxanes, vinyl terminated phenylmethylsiloxane-diphenyidimethylsiloxane copolymers, vinyl terminated polydimethylsiloxanes and methacrylate, and acrylate functional siloxanes. In other embodiments the lens-forming materials can be a hydrogel or a hydrophobic acrylic, such as the AcrySof® acrylic. Use of elastic/flexible materials can also enable the IOL 10 or optic body 20 to be folded upon itself during implantation, thereby decreasing the size of the incision required to insert the IOL 10 into the capsular bag 2. The present disclosure contemplates that fluid optic body 20 and the second optic body 30 may be constructed of the same or different materials.

In certain embodiments, fluid optic body 20, second optic body 30, and struts 40 can comprise a unitary body formed of the same material throughout, though these portions may vary in thickness in order to provide for desired movement of the IOL 10, as otherwise discussed herein. For example, second optic body 30 may be thicker than struts 40 and sidewall 26 such that the second optic body 30 provides structural support to the IOL 10 during axial compression of the capsular bag and efficiently transfers the axial force to the struts 40, the sidewall 26, and ultimately to the deformable optical membrane 22. Likewise, the posterior optic 24 may be thicker relative to the sidewall 26 and deformable optical membrane 22 such that the posterior optic 24 may also provide structural support for the IOL 10 upon axial compression of the capsular bag. Additionally, this configuration may allow the sidewall 26 to flex or rotate in response to the deformation of struts 40, thereby tensioning/stretching the deformable optical membrane 22.

In certain embodiments, various portions of the IOL 10 may be made of materials of different stiffness to provide for desired movement of the IOL 10, as otherwise discussed herein. For example, the deformable optical membrane 22 may be made of an elastomeric material having a low modulus, while the second optical body 30 and posterior optic 24 may be of a more rigid material.

The various components of IOL 10 may each have any suitable configuration facilitating accommodation as described herein. For example, fluid optic body 20 and second optic body 30 may each have substantially circular cross sections. Alternatively, fluid optic body 20 and second optic body 30 may each have non-circular cross sections (e.g., oval or elliptical cross-section). Additionally, the sidewall 26 of fluid optic body 20 may have any suitable configuration that facilitates rotation/flexion in response to deformation of the attached struts 40. For example, the sidewall 26 may define a diameter 27 of the fluid optic body 20, and the deformable optical membrane 22 may span that diameter. Upon axial compression of the capsular bag (in the direction indicated by the arrows in FIG. 2), struts 40 may impart a force on the sidewall 26, thereby causing deformation of the sidewall 26 in a manner that cause the diameter 27 defined by the sidewall to increase. In particular, the sidewall 26 may deform such that at least a portion of the sidewall 26 rotates about a pivot. This increase in diameter 27 of sidewall 26 may cause a change in the radius of curvature of the deformable optical membrane 22 (e.g., by radially stretching the deformable optical membrane 22).

The present disclosure contemplates that the term "diameter" may encompass multiple diameters in the case of a fluid optic body 20 having a non-circular cross section (e.g., an elliptical cross section having a transverse and conjugate diameter). Moreover, when the term "diameter" encompasses multiple diameters, deformation of the sidewall in a manner that increases the diameter defined by the sidewall to increase may encompass an increase in one or more of those diameters.

The optical fluid contained within the cavity 28 of IOL 10 may be any suitable fluid and may include, for example, an incompressible or substantially incompressible fluid exhibiting an index of refraction different that the fluid surrounding the IOL 10. As a result, light passing through the IOL 10 may undergo refraction at both the deformable optical membrane 22 and the posterior optic 24, the level of refraction being dependent upon the shape of the boundary between the optical fluid and the external fluid (i.e., the shape of the deformable optical membrane 22 and the posterior optic 24 relative to the optical axis(A)). Exemplary suitable fluids for use in the cavity 28 include fluids with an index of refraction higher than water, for example, an index of refraction greater than 1.3. In certain embodiments, the fluid may exhibit an index of refraction greater than 1.36 or greater than 1.38. In other embodiments, the index of refraction may be in the range of about 1.3 to about 1.8, in the range of about 1.36 to about 1.70, or in the range of about 1.38 to about 1.60. Suitable fluids may include saline, hydrocarbon oils, silicone oils, and silicone gels.

The optical fluid may be disposed within the cavity 28 during fabrication of the IOL 10, after fabrication but before implantation of the IOL 10, or after implantation of the IOL 10. For example, the optic body 20 may include a fill port that can be sealed or plugged after filling the cavity 28. Additionally or alternatively, the optical fluid may be injected through the optic body 20 and the optic body 20 may be self-sealing.

The plurality of struts 40 may have any suitable configuration facilitating accommodation of the IOL 10 as described herein. For example, each of the plurality of struts 40 may generally extend between the fluid optic body 20 and the second optic body 30 (thereby coupling the fluid optic body 20 to the second optic body 30) and may be configured to move or deform in response to axial compression of the capsular bag (as described in detail below). In particular, as shown in FIG. 1, each of the plurality of struts 40 may extend in a direction substantially parallel to the optical axis (A) and couple a point or region on the circumference of the fluid optic body 20 to a point or region on the circumference of the second optic body 30. Although a particular number of struts 40 are depicted, the present disclosure contemplates any suitable number of struts 40 facilitating to translation of axial compression of the capsular bag into modification of the curvature of at least the deformable optical membrane 22.

In certain embodiments, each of the struts 40 may be curved. As a result, the axial force imparted by the capsular bag may tend to increase radial bowing of the struts 40. As a result, the maximum diameter of the IOL 10 in the disaccommodated state may be increased.

In certain embodiments, struts 40 may have cross-sectional areas that varies with length so as to provide additional support and/or to provide for the movement of the struts 40 as discussed herein. For example, portions of a struts 40 that are closer to the fluid optic body 20 (e.g., the posterior end of the strut 40) may be thinner relative to the portions of the strut 40 closer to the second optic body 30 (e.g., the anterior end of the strut). As a result, the posterior end of the strut 40 may move in response to axial compression so as to increase the deformation of the deformable optical membrane 22.

In certain embodiments, adjacent struts 40 may be coupled to one another via a ring-like structure 46 disposed around the circumference of the IOL 10. Ring 46 may increase stability of the IOL 10 within the capsular bag and/or improve the uniformity of the force exerted on the struts 40 and deformable membrane 22 as the IOL 10 is axially compressed. Additionally, the axial force exerted on the second optic body 30 may be more evenly distributed between the struts 40 due to their coupling with the ring 46, and the ring 46 may provide additional support to the struts 40 at a location between the fluid optic body 20 and the second optic body 30 in which stress on the struts 40 during axial compression is concentrated.

In certain embodiments, the fluid optic body 20, the second optic body 30, and the struts 40 may each be dimensioned such that, in its resting state (as shown in FIG. 2), the IOL 10 may have a length along the optical axis (A) that is slightly larger than the anterior-to-posterior depth of the capsular bag. As a result, tension exerted by the capsular bag on the IOL 10 upon implantation may substantially maintain the IOL 10 in a desired position. Additionally, the fluid optic body 20, the second optic body 30, and the struts 40 may each be dimensioned such that the surface area that engages the anterior and posterior surfaces of the capsular bag is maximized while minimizing the overall volume of the IOL 10. For example, the radial dimensions of the IOL 10 may be slightly smaller than diameter of the capsular bag to help maximize the transfer of energy to the IOL 10 by minimizing loss of energy due to lateral stretching of the IOL 10.

Figure 3A:
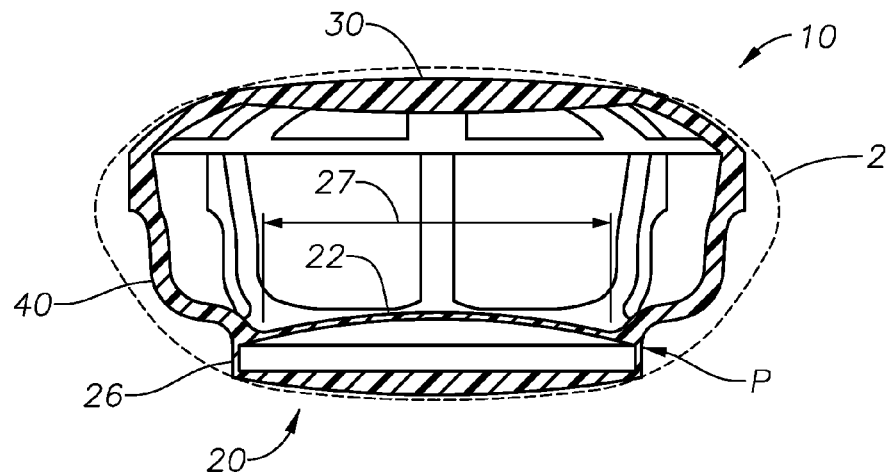
FIG. 3A is a cross-sectional view of the exemplary lens of FIG. 1, depicting the lens in its accommodated (close vision) state within the capsular bag.
Figure 3B:
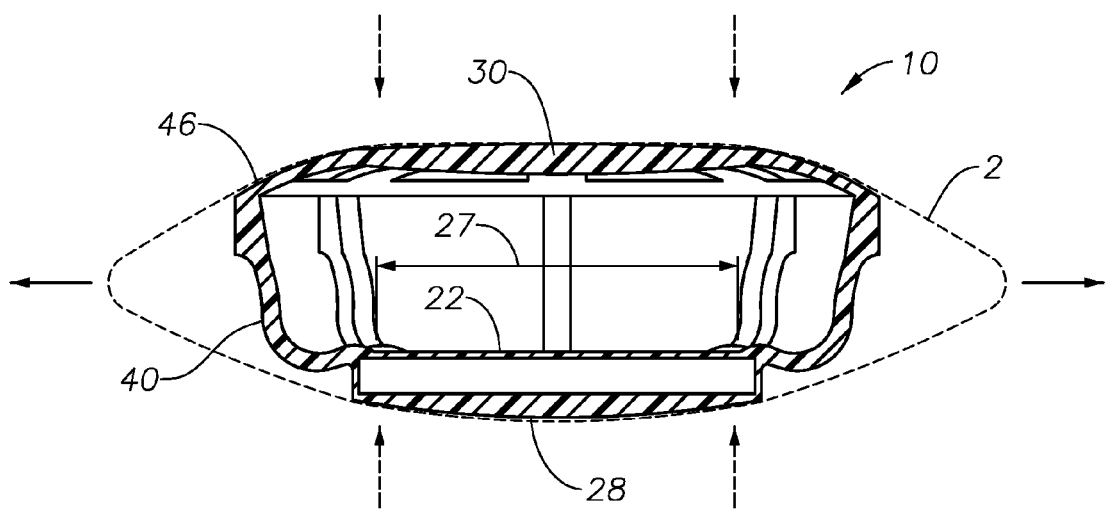
FIG. 3B is a cross-sectional view of the exemplary lens of FIG. 1, depicting the lens in its disaccommodated (near vision) state within the capsular bag.

Movement of the exemplary IOL 10 will now be described as the capsular bag 2 goes from an accommodated state, as shown in FIG. 3A, to a disaccommodated state, as shown in FIG. 3B. With reference first to FIG. 3A, the IOL 10 and capsular bag 2 are depicted in their accommodated state during which the ciliary muscles are contracted such that zonules extending between the ciliary muscles and the capsular bag 2 are slack. As a result, there exists little radial tension on the capsular bag 2. As discussed above, IOL 10 may be sized such that, in this state, the fluid optic body 20 and the second optic body 30 may each be in contact with the capsular bag 2, but the capsular bag 2 may exert a minimum amount of axial force on the IOL 10. This minimum amount of axial force may help maintain the IOL 10 in a desired position within the capsular bag 2.

Upon relaxation of the ciliary muscles, the zonules will exert radial tension on the capsular bag 2 (as indicated by the solid arrows in FIG. 3B), which causes axial compression of the capsular bag 2 (as indicated by the broken arrows). As a result, the capsular bag 2 may exert a force on the IOL 10 (specifically fluid optic body 20 and second optic body 30), and this force may cause a decrease in the separation distance between fluid optic body 20 and second optic body 30. This decrease in the separation distance between fluid optic body 20 and second optic body 30 may contribute to the optical power change of the IOL 10. However, the primary factor affecting the optical power change of the IOL 10 may be the curvature change of the deformable optic membrane 22 resulting from deformation of struts 40, as discussed further below.

As is illustrated by comparing FIGS. 3A and 3B, the maximum diameter of IOL 10 (e.g., the diameter measured at the ring 46) may increase due deformation of struts 40 resulting from axial compression of the capsular bag 2. In particular, the posterior-curved portions of the struts 40 located adjacent to fluid optic body 20 may move radially and/or posteriorly (e.g., through rotation about the fluid optic body 20). Because the posterior-most ends of struts 40 are coupled to the sidewall 26, such deformation of the struts 40 may impart a force upon the sidewall 26 and cause deformation of the sidewall 26. For example, at least a portion of the sidewall 26 may rotate outward about a pivot such that the diameter 27 defined by the sidewall 26 increases. In certain embodiments, the portion of sidewall 26 defining diameter 27 (i.e., the point at which sidewall 26 and deformable optical membrane 22 intersect) may anteriorly raise the periphery of the deformable optic membrane 22. Deformation of sidewall 26 in a manner that increases diameter 27 may increase tension and radial stretching of the deformable membrane 22. As a result, the deformable optical membrane 22 may exhibit a flatter profile (e.g., a larger radius of curvature). Additionally, the distance between the deformable optical membrane 22 and the posterior optic 24 (along the optical axis (A)) may be decreased. As the radial force on the capsular bag 2 is relaxed, the capsular bag 2 and IOL 10 may return to their biased configuration shown in FIG. 2.

Figure 4A:
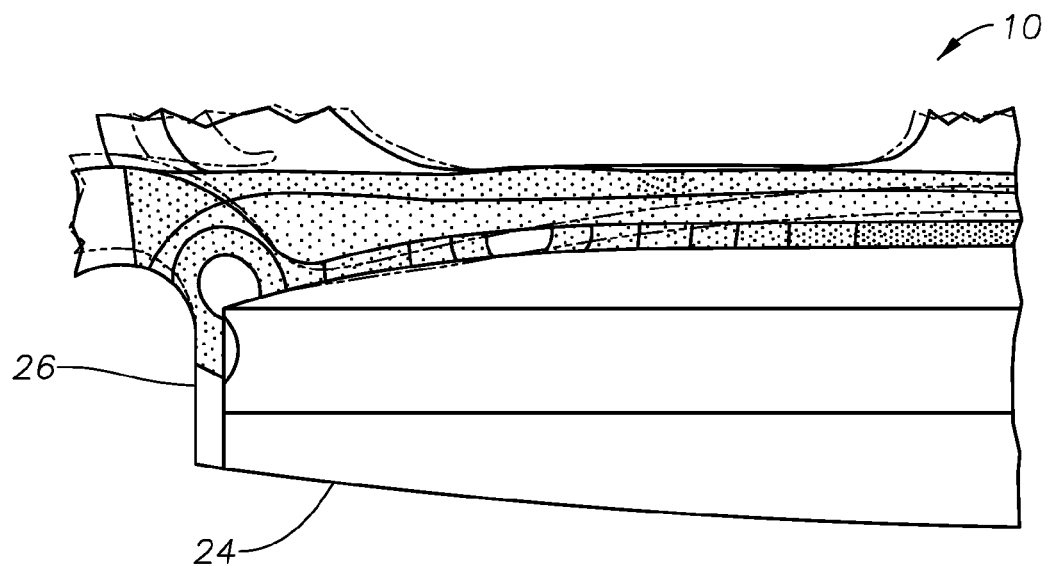
FIG. 4A is a simulation of the pivoting of the struts and the curvature change of the deformable optical membrane of the exemplary lens of FIG. 1 as it moves from an accommodated state to a disaccommodated state.
Figure 4B:
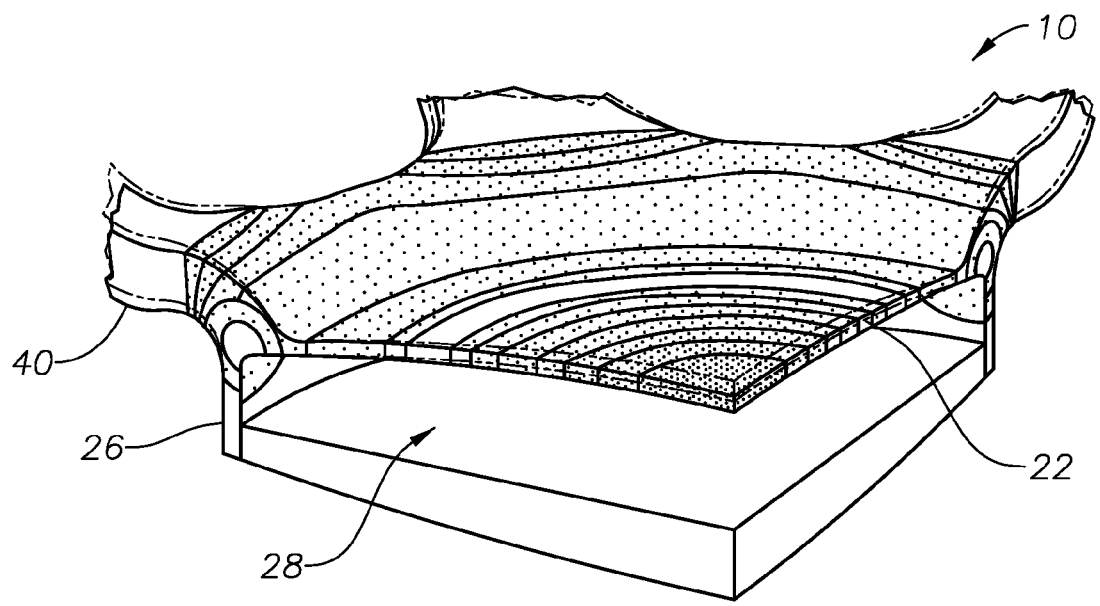
FIG. 4B is another view of the simulation of the pivoting of the struts and the curvature change of the deformable optical membrane of the exemplary lens of FIG. 1 as it moves from an accommodated state to a disaccommodated state.

With reference now to FIGS. 4A and 4B, finite element analysis of exemplary simulated movement of the IOL 10 is depicted as the IOL 10 moves from its resting or accommodated state (as shown in phantom outline) to its disaccommodated state (as shown in solid color). Upon axial compression of the capsular bag, the axial compressive force on the IOL 10 increases, initiating movement of the struts 40 and deformation of the sidewall 26. This movement of struts 40 transfers at least a portion of the force exerted on IOL 10 to the sidewall 26, which in turn transfers at least a portion of that force to deformable optical membrane 22. The resulting stress on deformable optical membrane 22 is at a maximum along the optical axis as the deformable optical membrane 22 is pulled from all sides. As compression continues, the struts 40 rotate further and the cavity 28 containing the optical fluid changes shape as the deformable optical membrane 22 becomes flatter.

As the thickness of the sidewall 26 increases and/or its height decreases, the overall power change of the IOL 10 during compression may decrease or a greater axial compressive force to achieve the same deformation may be required. In order to achieve maximum power change, the thickness of the sidewall 26 (i.e., in a radial direction) may be significantly less than its height (i.e., along the optical axis (A)). Additionally, increased thickness of the junction of the deformable optical membrane 22 and the sidewall 26 may help in distributing the deformation from the struts 40 more uniformly on the optic membrane 22, which may reduce the number of struts 40 needed without inducing optical aberrations in the deformable optical membrane 22.

The present disclosure contemplates that the thickness of the deformable optical membrane 22 may be manipulated (e.g., increased, decreased, and/or varied about its area) so as to maintain good visual acuity and high power change throughout accommodation. For example, a convex deformable optical membrane 22 (i.e., a membrane in which the central portion is thicker than the periphery) with a low power may reduce aberrations during accommodation. Alternatively, if the deformable optical membrane 22 is flat (i.e., the membrane exhibits a substantially constant thickness), it will deform more easily in the central part than the periphery. Additionally, the present disclosure contemplates that each surface of the IOL 10 within the optical aperture lens can be spherical or aspheric so as to alter the optical properties of light traversing therethrough. For example, the various surfaces of the second optic body 30 provide various locations to include complex optical designs, in accordance with that process as known in the art and modified in accordance with the present teachings.

The above-described IOL 10 may be fabricated using any suitable techniques known in the art and modified in light of the present teachings. For example, IOL 10 may be injection molded such that the struts 40 and deformable optical membrane 22 can be biased to the position shown in FIG. 2. That is, in the absence of substantial external forces (e.g., in its free form outside the eye), the IOL 10 can be configured to maintain a radius of curvature approximate its shape in an accommodated state. Accordingly, the struts 40 would tend to return to this biased position upon removal of or relaxation of the axial compressive force (e.g., as the capsular bag goes from its disaccommodated configuration to its accommodated configuration). This biased configuration may especially aid those patients in which the ciliary bodies have lost some of their contractility or the capsular bag 2 has lost some of its elasticity, for example, due to age.

Figure 5:
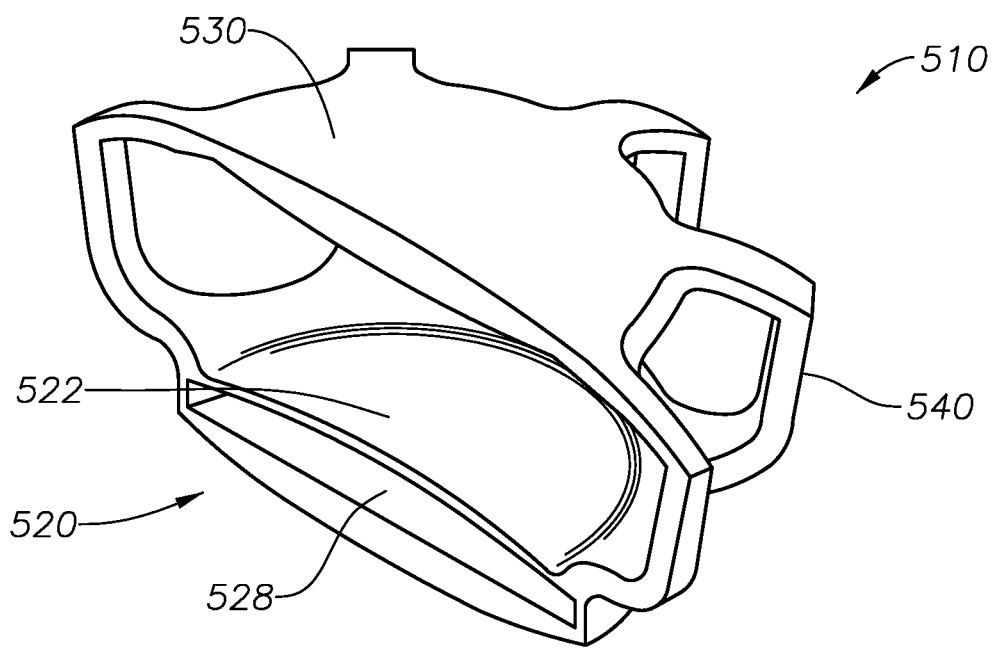
FIG. 5 is a perspective, cross-sectional view of another exemplary curvature-changing, accommodative intraocular lens, according to certain embodiments of the present disclosure.

With reference now to FIG. 5, another exemplary IOL 510 is depicted. The IOL 510 is substantially similar to the IOL 10 depicted in FIG. 1 in that it includes a fluid optic body 520, a second optic body 530, and a plurality of struts 540 extending therebetween. Similarly, the fluid optic body 520 defines a cavity 528 for containing a fluid and is configured to change shape upon axial compression of the IOL 510 due to movement of the struts 540. The IOL 510 differs, however, in that adjacent struts 540 are not coupled to one another at a location between fluid optic bodies 520 and second optic body 530 (e.g., via a ring 46 as shown in FIG. 1). Although the ring 46 can provide stability in some aspects, a lens such as IOL 510 lacking such a ring may ease implantation (e.g., by allowing the IOL 510 to be folded into a more compact shape) and may ease viscoelastic removal. In certain embodiments, the dimensions of IOL 510 may be have a greater overall diameter relative to IOL 10 so as to extend more radially within the capsular bag, thereby increasing stability of the IOL 510 (e.g., by reducing rotation) following implantation.

Figure 6:
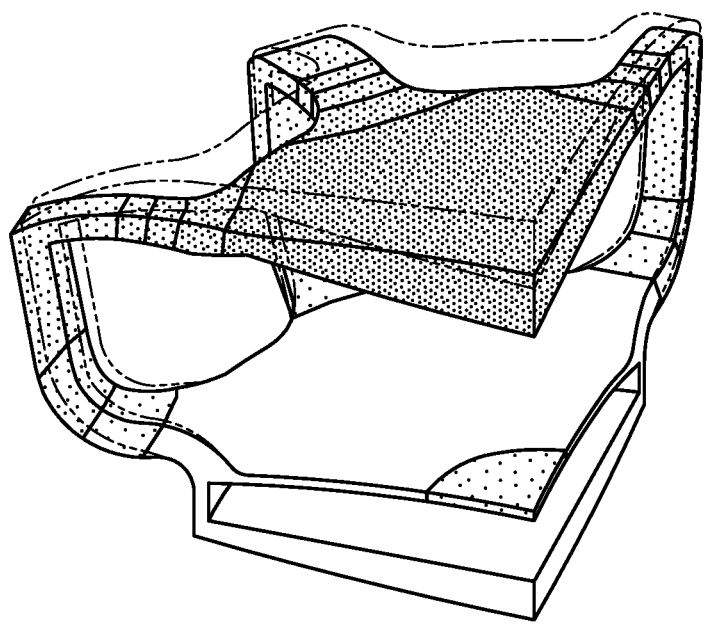
FIG. 6 is a simulation of the movement of the exemplary lens of FIG. 6 as it moves from its resting or accommodated state to its disaccommodated state.

With reference now to FIG. 6, finite element analysis of exemplary simulated movement of the IOL 510 is depicted as the lens 510 moves from its resting or accommodated state (as shown in phantom outline) to its disaccommodated state (as shown in solid color). Upon axial compression of the capsular bag, the axial compressive force on the IOL 510 initiates movement of the second optic body 530 and thus rotation and/or bowing out of struts 540. This rotation results in a radial force applied to the deformable optical membrane 522 such that the cavity 528 containing the optical fluid changes shape, thereby altering the power of the fluid optic body 520.

Figure 7:
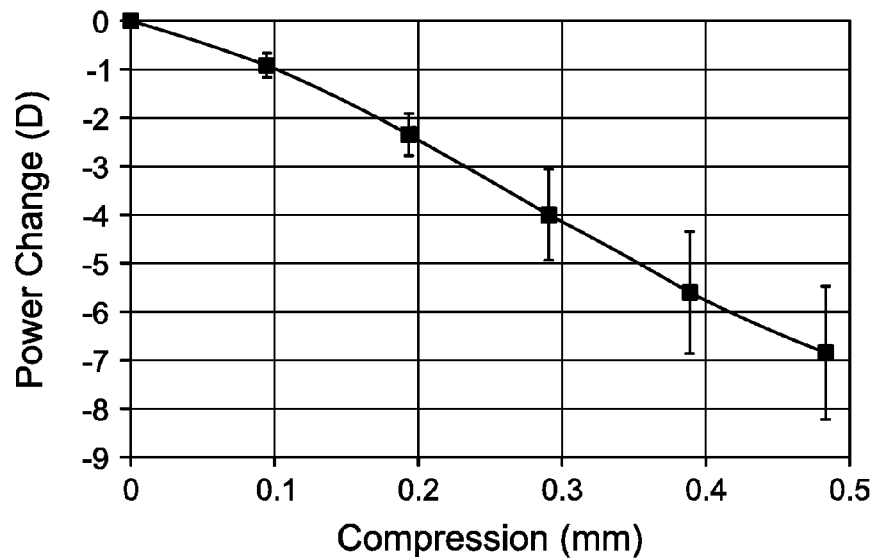
FIG. 7 is a plot depicting the power change of the exemplary lens of FIG. 6 as it moves from its resting or accommodated state to its disaccommodated state.

With reference now to FIG. 7, an exemplary simulation depicts the optical power change of the exemplary IOL 510 as it moves from its accommodated state to its disaccommodated state. As the lens 510 is compressed from its accommodated state (compression=0 mm) to its disaccommodated state (compression=0.5 mm), the IOL 510 exhibits an optical power change of −7 diopter, which is a decrease in the focusing power (for far vision as the light rays from far objects are more parallel relative to those from near objects).

Figure 8:
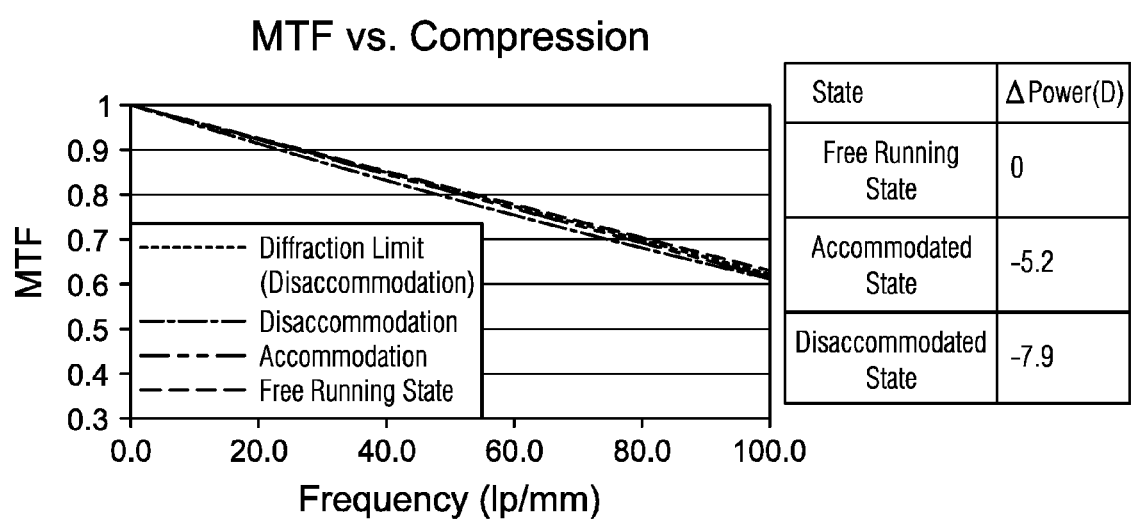
FIG. 8 depicts data showing the modulation transfer function and power change of the exemplary lens as shown in FIG. 1.

With reference now to FIG. 8, a simulated modulation transfer function (MTF) and power change is depicted for a lens in accordance with FIG. 5. The simulation was performed with a 3 mm pupil and a model eye. In the simulation, a simple spherical convex type membrane is used. Since dynamic aberrations are reasonably compensated by the membrane, all MTF curves are close to the diffraction limited MTF over ~8 D power change.

Figure 9A:
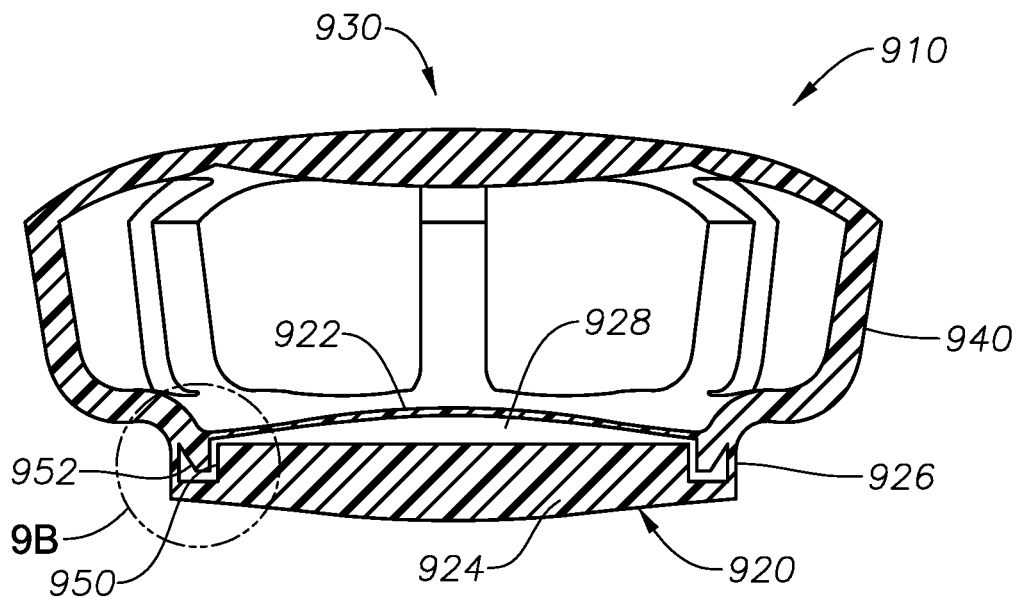
FIGS. 9A-9B are cross-sectional views of another exemplary curvature-changing, accommodative intraocular lens, according to certain embodiments of the present disclosure.
Figure 9B:
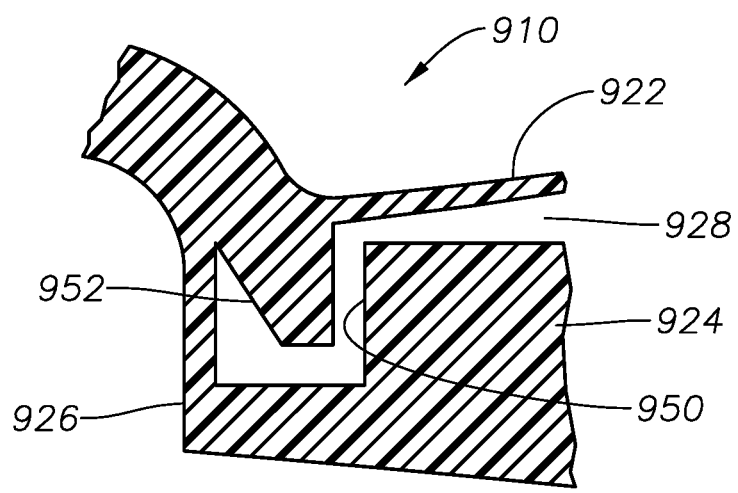
Figure 10A:
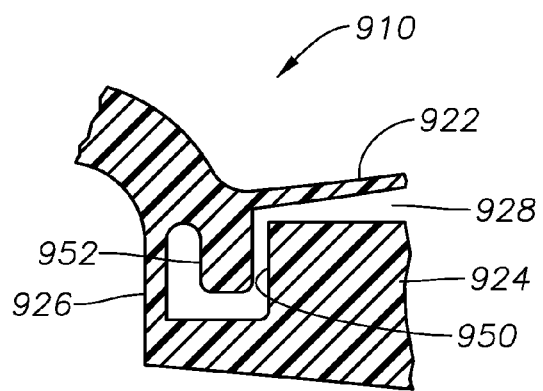
FIGS. 10A-10D are cross-sectional views of alternative configurations of the mechanical block feature of the exemplary lens of FIG. 9, according to certain embodiments of the present disclosure.
Figure 10B:
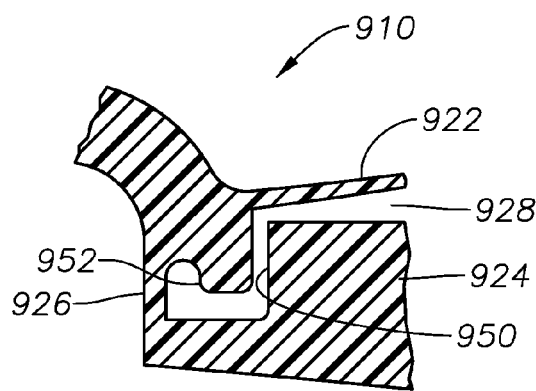
Figure 10C:
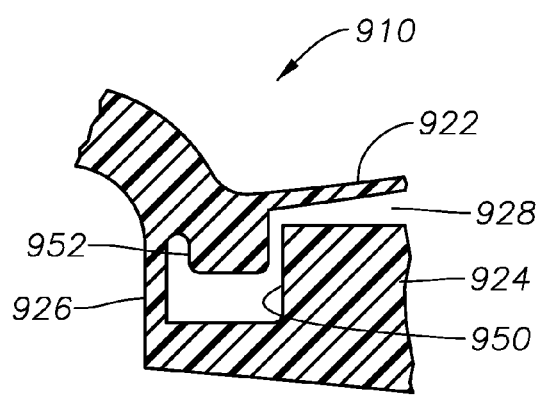
Figure 10D:
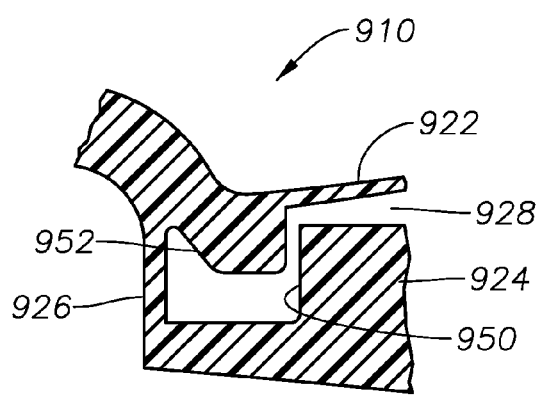
Figure 13:
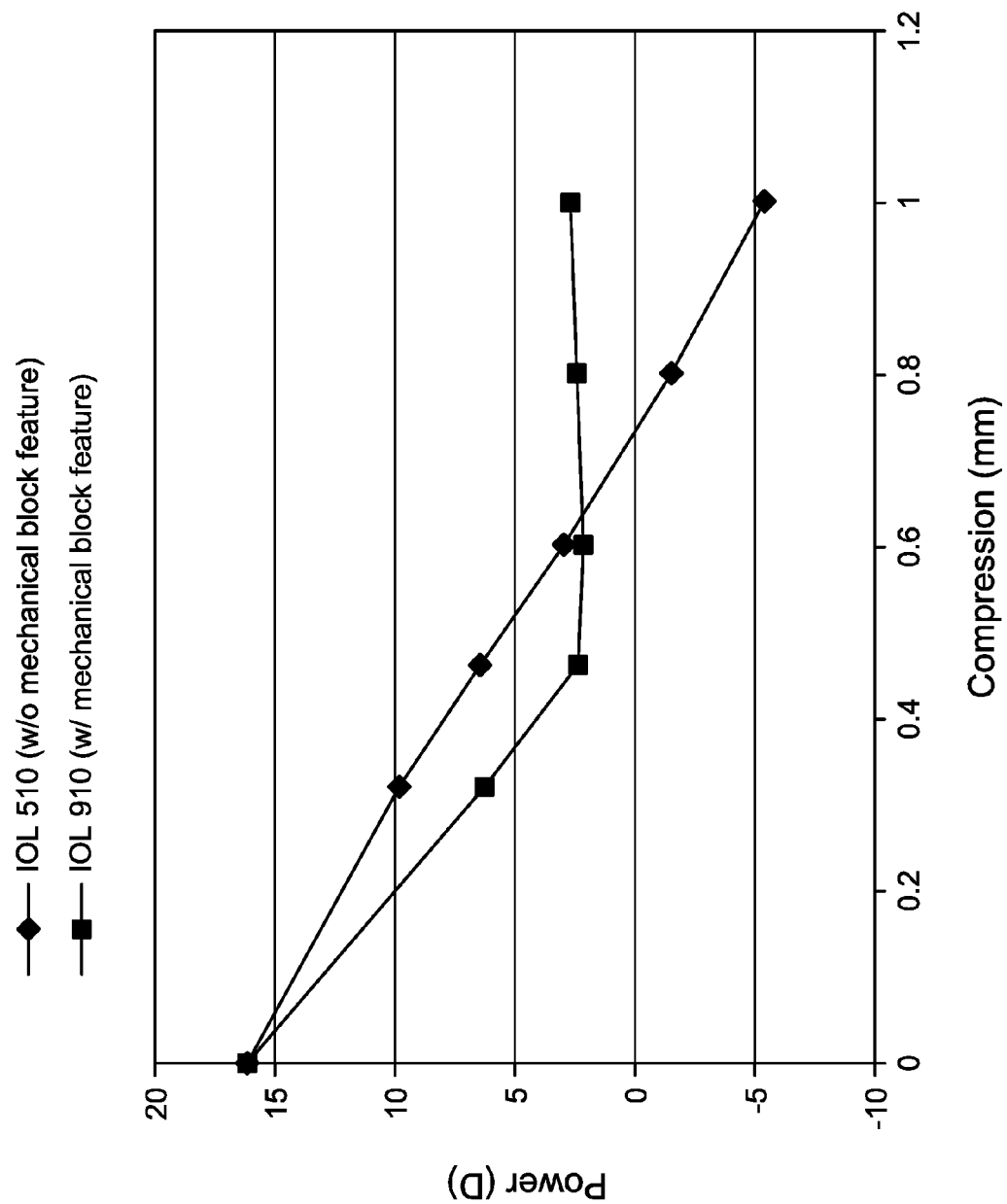
FIG. 13 is a plot illustrating the optical power of the exemplary lenses of FIGS. 5 and 9A-9B versus compression of the capsular bag.

With reference now to FIGS. 9A-9B, another exemplary IOL 910 is depicted. IOL 910 may be substantially similar to IOL 510 depicted of FIG. 5, but differing in that the IOL 910 additionally includes a mechanical block feature configured to interfere with the curvature change that can be exhibited by the deformable optical membrane 922. In particular, the mechanical block feature may consist of two primary components: (1) a central protrusion portion 950 of the posterior optic 924 extending anteriorly into the cavity 928, and (2) a ring-shaped protrusion 952 extending posteriorly from the deformable optical membrane 922 into a portion of the cavity 928 between the sidewall 926 and the central protrusion 950 of the posterior optic 924. This combination of components may constrain movement of the deformable optical membrane 922 and define a fixed minimum refractive power (as described in further detail below). In addition to defining a fixed minimum refractive power, the mechanical block feature may also be advantageous in that it reduces the total fluid volume of cavity 928, increases power change at low levels of compression (as illustrated in FIG. 13), and decreases the amount of higher order aberrations induced during compression (due at least in part to the structural stability added to the periphery of the deformable optical membrane 922 by ring-shaped protrusion 952).

Although the components 950/952 of the mechanical block feature are shown as having particular shapes and relative orientations, the present disclosure contemplates that the components 950/952 of the mechanical block feature may each have any suitable shape. For example, FIGS. 10A-10D illustrate alternatively shaped components 950/952 of the mechanical block feature illustrated in FIG. 9. In particular, as illustrated, the components 950/952 may have various widths and/or volumes, edges of the components 950/952 may be rounded, and/or draft angles may be applied to various surfaces of components 950/952.

Figure 11A:
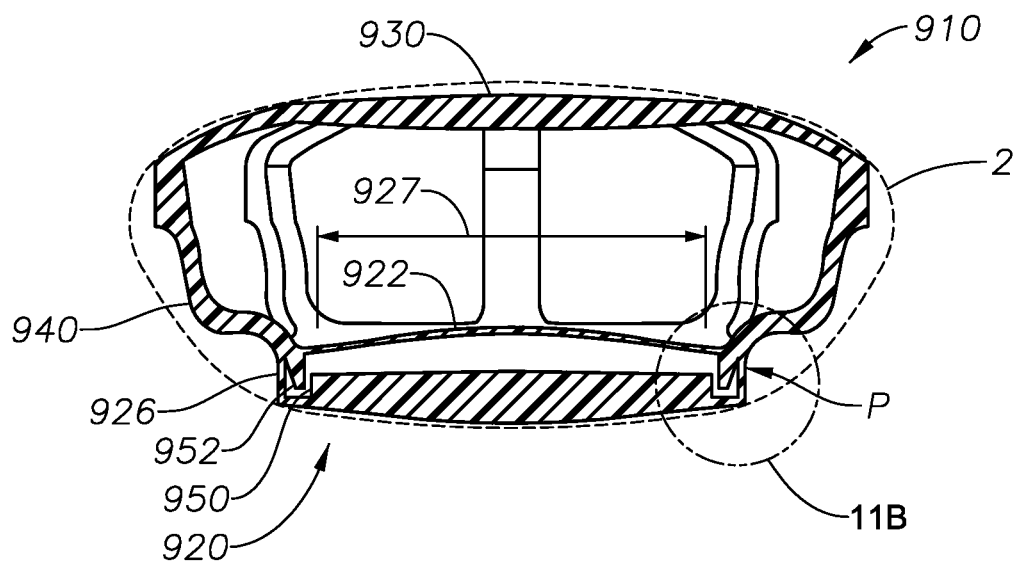
FIGS. 11A-11B are cross-sectional views of the exemplary lens of FIG. 9, depicting the lens in its accommodated (close vision) state within the capsular bag.
Figure 11B:
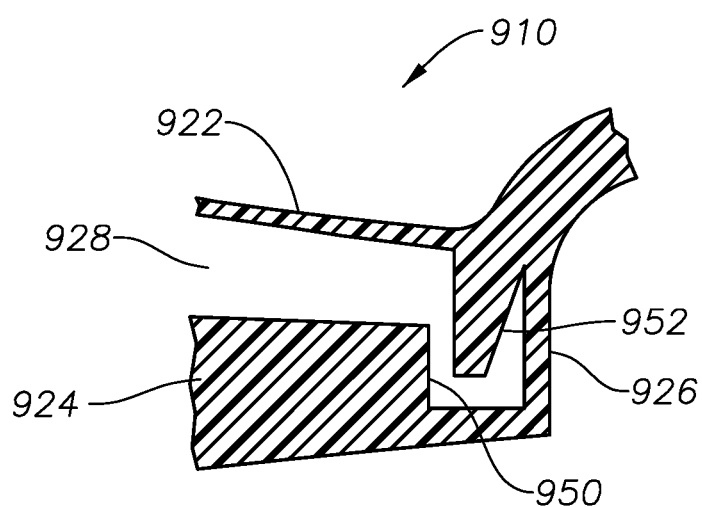
Figure 12A:
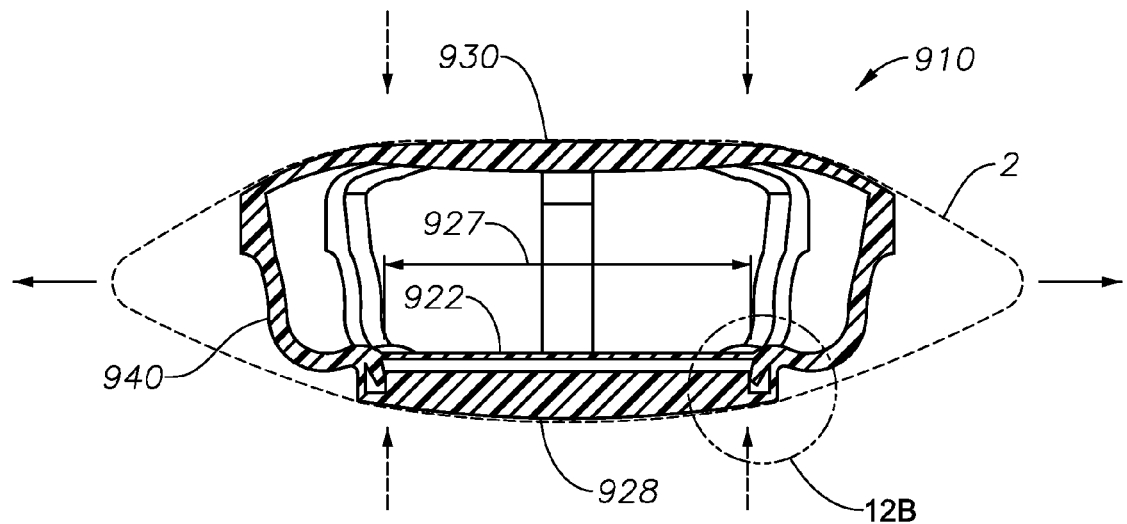
FIG. 12A-12B are cross-sectional view of the exemplary lens of FIG. 9, depicting the lens in its disaccommodated (near vision) state within the capsular bag.
Figure 12B:
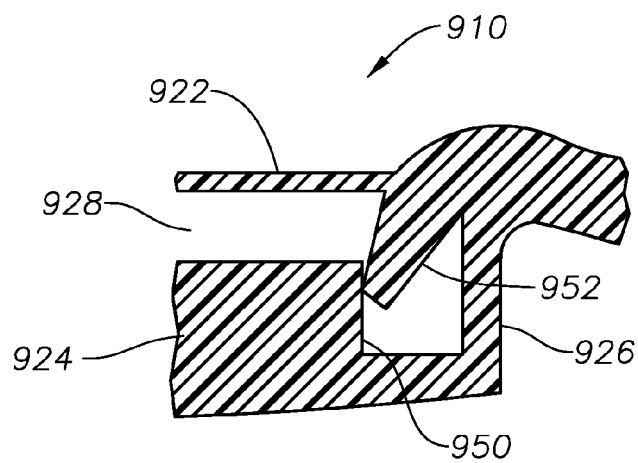

FIGS. 11A-11B and 12A-12B illustrate the effect of the mechanical block feature as the IOL 910 changes power axial compression of the capsular bag 2. In particular, FIGS. 11A-11B illustrate IOL 910 in an accommodated state (maximum refractive power) and FIGS. 12A-12B illustrate IOL 910 in a disaccommodated state (minimum refractive power).

As discussed above with regard to FIGS. 3A-3B, axial compression of the capsular bag 2 may cause the posterior-curved portions of the struts 940 located adjacent to fluid optic body 920 to move radially and/or posteriorly (e.g., through rotation about the fluid optic body 920). Because the posterior-most ends of struts 940 are coupled to the sidewall 926, such deformation of the struts 940 may impart a force upon the sidewall 926 and cause deformation of the sidewall 926. For example, at least a portion of the sidewall 926 may rotate outward about a pivot such that the diameter defined by the sidewall 26 increases. Such deformation of sidewall 926 may increase tension and radial stretching of the deformable membrane 922. In addition, rotation about the pivot point during deformation of sidewall 926 may cause corresponding rotation of ring-shaped protrusion 952 such that the space between ring-shaped protrusion 952 and central protrusion portion 950 is decreased. As compression continues, ring-shaped protrusion 952 may contact central protrusion portion 950 and define a maximum deformation of sidewall 926 as well as a maximum radial stretching of the deformable membrane 922. As a result, ring-shaped protrusion 952 and central protrusion portion 950 may collectively define a minimum refractive power for IOL 910.

FIG. 13 is a plot illustrating the optical power of IOLs 510 and 910 versus compression of the capsular bag 2. As illustrated, the mechanical block feature of IOL 910 may increase the rate of optical power change at low compression levels (highlighted by the increased slope of the plot related to IOL 910 for low compression levels). Additionally, the mechanical block feature of IOL 910 may define a minimum refractive power for IOL 910 despite increased compressive force (as the mechanical block feature may provide an equivalent resistive force that prevents further compression.

As noted above, the IOLs described herein generally provide a space between the optic bodies and struts within which a solid lens can be disposed. Whereas the curvature of the deformable optical membrane (e.g., deformable optical membrane 22 of FIG. 1) is generally responsible for the optical power of the IOL, a solid lens disposed within the space can additionally provide for power change or other features (e.g., spherical, aspheric, toric features), as is known in the art. To further aid delivery, the solid lens can also be elastomeric or foldable to ease insertion into the capsular bag. Additionally or alternatively, a second optic body of the IOLs described herein can provide for such spherical, aspherical, or toric features, as noted above.

In use, the exemplary accommodative intraocular lenses described herein are adapted to be inserted in the human eye using conventional surgical techniques modified in accordance with the present teachings. Typically, the natural crystalline lens is first removed and the IOL can be folded into a compact size for insertion through an incision or opening in the capsular bag. Following insertion, a single piece IOL (e.g., IOL 10) can be manipulated to assume its proper position in the capsular bag, as described above. Alternatively, an IOL in which multiple components are delivered to the capsular bag independently can be assembled in situ (e.g., by coupling the struts 40 to a fluid optic body 20 delivered independently). In some aspects, the IOLs described herein can be implanted in the capsular bag without optical fluid contained within the cavity of the fluid optic body such that the method for implantation can further include filling the cavity with the optical fluid while the lens is disposed within the eye (e.g., via injection). In this manner, implantation of the exemplary IOLs described herein can aid in restoring natural vision by providing an accommodative, curvature-changing refractive lens that mimics how the natural crystalline lens changes shape in response to movement of the ciliary bodies to variously bend incoming light onto the retina depending on the desired focal point.

The term intraocular lens or "IOL" is used herein to refer to any lens or lens component adapted to be inserted into a patient's eye. Such a lens can be phakic or aphakic (also referred to in the art as pseudophakic) to restore, improve, or partially correct vision. Phakic lenses are used in conjunction with the natural lens of an eye to correct refractive errors such as myopia (near-sightedness), hyperopia (far-sightedness) and astigmatism, coma or other higher order refractive errors (blurred vision due to poor light focusing on the retina due to an irregularly shaped cornea or, in some instances, an irregularly shaped natural lens). An aphakic or pseudophakic lens is inserted in the eye subsequent to removal of the natural lens due to disease, e.g., a cataract or clouding of the natural lens. The aphakic or pseudophakic lens can also restore, improve, or partially correct vision by providing a power comparable to that of the natural lens and can also correct myopia, hyperopia or other refractive errors. Either type of lens may be implanted in the anterior chamber in front of the iris or in the posterior chamber behind the iris and in front of the natural lens or in the region where the natural lens was before removal.

It will be appreciated that various of the above-disclosed and other features and functions, or alternatives thereof, may be desirably combined into many other different systems or applications. It will also be appreciated that various presently unforeseen or unanticipated alternatives, modifications, variations or improvements therein may be subsequently made by those skilled in the art which alternatives, variations and improvements are also intended to be encompassed by the following claims.

The invention claimed is:

1. An intraocular lens configured to be implanted within a capsular bag of a patient's eye, the lens comprising:
   a fluid optic body comprising a cavity for containing an optical fluid, the cavity defined by:
      a sidewall extending around the cavity and defining a diameter of the cavity;
      a deformable optical membrane intersecting the sidewall around an anterior circumference of the sidewall and spanning the diameter of the cavity, the deformable optical membrane configured to extend across the optical axis of the patient's eye;
      a posterior optic intersecting the sidewall around a posterior circumference of the sidewall, wherein:
         the posterior optic comprises a central protrusion extending anteriorly into the cavity; and
         the deformable optical membrane comprises a ring-shaped protrusion extending posteriorly into a space between the sidewall and the central protrusion of the posterior optic; and
   a second optic body spaced a distance apart from the fluid optic body and configured to extend across the optical axis of the patient's eye; and
   a plurality of struts extending from the sidewall and coupling the fluid optic body to the second optic body, the struts being configured such that axial compression of the capsular bag causes the plurality of struts to deform the sidewall in a manner that increases the diameter of the cavity such that a curvature of the deformable optical membrane is modified, wherein contact between the ring-shaped protrusion of the deformable optical membrane and the central protrusion of the posterior optic defines a maximum modification to the curvature of the deformable optical membrane.

2. The intraocular lens of claim 1, wherein the fluid optic body is configured to be disposed in contact with a first surface of the capsular bag and the second optic body is configured to be disposed in contact with a second surface of the capsular bag.

3. The intraocular lens of claim 1, wherein the deformation of the sidewall in a manner that increases the diameter of the cavity causes an increase in tension on the deformable optical membrane.

4. The intraocular lens of claim 3, wherein the deformation of the sidewall in a manner that increases the diameter of the cavity causes the deformable optical membrane to stretch radially.

5. The intraocular lens of claim 1, wherein the struts are configured such that axial compression of the capsular bag causes deformation of the struts.

6. The intraocular lens of claim 5, wherein the deformation of the struts comprises each of the struts bowing outward relative to the optical axis of the patient's eye.

7. The intraocular lens of claim 5, wherein the deformation of the struts comprises a radius of curvature of each of the struts decreasing.

8. The intraocular lens of claim 1, wherein the struts are configured such that the axial compression of the capsular bag causes the plurality of struts to deform the sidewall in a manner that increases the diameter of the cavity such that the curvature of the deformable optical membrane is increased.

9. The intraocular lens of claim 1, wherein the struts are configured such that axial compression of the capsular bag causes the plurality of struts to deform the sidewall in a manner that decreases a distance between the fluid optic body and the second optic body along the optical axis.

10. The intraocular lens of claim 1, wherein the deformation of the sidewall comprises rotation of at least a portion of the sidewall about a pivot.

11. The intraocular lens of claim 1, wherein each of the plurality of struts comprises a curved portion that is concave relative to the optical axis.

12. The intraocular lens of claim 1, wherein the second optic body comprises a solid optic.

13. The intraocular of claim 1, wherein the second optic body comprises a second fluid optic body.

14. The intraocular lens of claim 1, wherein each of the plurality of struts are coupled to one another via a circumferential ring disposed between the fluid optic body and the second optic body.

15. The intraocular lens of claim 14, wherein the circumferential ring increases in diameter upon axial compression of the capsular bag.

16. The intraocular lens of claim 1, further comprising a solid lens disposed between the fluid optic body and the second optic body.

* * * * *